United States Patent [19]
Kofune et al.

[11] Patent Number: 5,483,069
[45] Date of Patent: Jan. 9, 1996

[54] VALIDATION APPARATUS FOR FLAT PAPER OBJECT

[75] Inventors: Shinichi Kofune; Kenya Kawabe, both of Kanagawa, Japan

[73] Assignee: Toyo Communication Equipment Co., Ltd., Kanagawa, Japan

[21] Appl. No.: 174,527

[22] Filed: Dec. 27, 1993

[51] Int. Cl.[6] .................................................. G01N 21/55
[52] U.S. Cl. .................................. 250/341.8; 250/341.1; 250/341.7
[58] Field of Search .............................. 250/341.8, 341.7, 250/341.1

[56] References Cited

U.S. PATENT DOCUMENTS

3,814,943  6/1974  Baker et al. ............................ 250/550
4,881,268  11/1989  Uchida et al. ................................ 382/7
4,935,628  6/1990  Martin et al. ......................... 250/338.1

*Primary Examiner*—Constantine Hannaher
*Attorney, Agent, or Firm*—Koda and Androlia

[57] ABSTRACT

An apparatus for validating bank bills including a reading apparatus for reading patterns on each bank bill to identify the bank bill by comparing the read data with pattern data of true bills stored in a memory, outer dimension detecting apparatus for detecting the outer dimensions of the bank bill, the memory also having stored therein the outer dimensions of true bills and classifying them into a plurality of groups so that only the pattern data of the bank bill corresponding to the detected outer dimension data is taken out from the memory to be compared with the pattern data read by the pattern reading apparatus.

1 Claim, 9 Drawing Sheets

| WIDTH (mm) / LENGTH (mm) | 70 ~ 75 | 75 ~ 80 | 80 ~ 85 |
|---|---|---|---|
| 150 ~ 160 | A B | C D | E |
| 160 ~ 170 | F G | H | I J |

VALIDATION APPARATUS FOR FLAT PAPER OBJECT

BACKGROUND OF THE INVENTION

1. Field of the Invention

The present invention relates to a validation apparatus for validating flat paper objects, and particularly to a bill validation apparatus, such as ATM (Automated Teller Machines) or CD (Cash Dispensers), for validating outer dimensions, watermark patterns, print patterns or the like elements on such objects.

2. Prior Art

Vending machines or money changing machines, such as ATM or CD, for delivering articles or coins have a bill validating apparatus for validating inserted bills built-in.

Figure 13A:
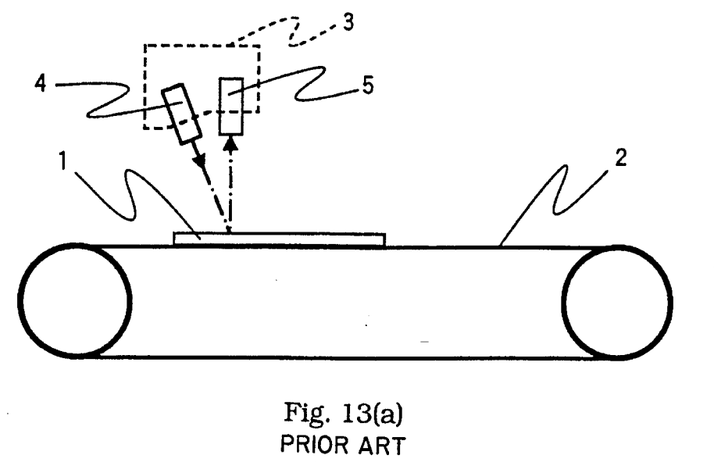
FIGS. 13(a) and 13(b) show structures of conventional bill validators, respectively.

As shown in FIG. 13(a), a bank bill 1 is transferred by a conveying means 2 such as a belt or the like. When the bill 1 reaches at a predetermined position, data on print patterns of the bill 1 are detected by a reflected light sensor 3 provided over the conveying means 2 as the bill is transferred. The detected data are compared with print pattern data of the corresponding true bills stored in a memory.

The sensor 3 comprises a light emitter 4 and a light detector 5. The light emitter 4 uses an LED or the like means as light source for generating a beam of visible light, and the light beam generated by the emitter 4 is irradiated and reflected on the surface of the bill 1.

Since the amount of reflected light changes in response to shades of colors of the print pattern, the light detector 5 detects the reflected light, and the pattern of the bill 1 is obtained by converting the amount of reflected light into an electric signal.

However, it is difficult to detect and reject forged bills that are produced by color copying machines by the conventional bill validating apparatus described above.

Figure 13B:
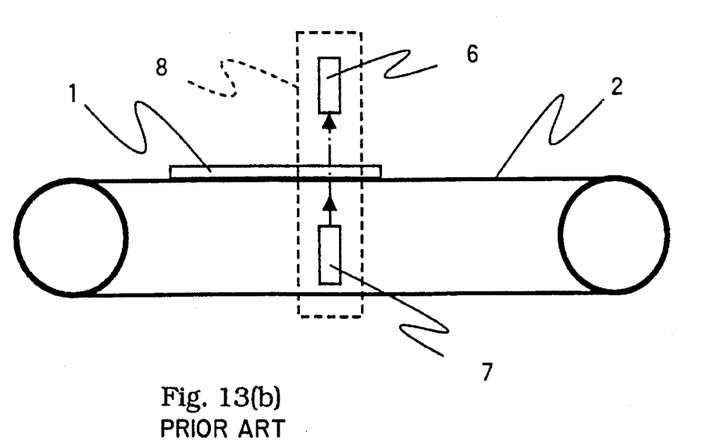

To solve that problem, it has been common to use a bill validating apparatus for detecting watermarks together with the print patterns of the bank bill 1 as shown in FIG. 13(b). The validating apparatus is provided with a transmitted light sensor 8, in place of the sensor 3, including a light detector 6 disposed above the conveying path of the bill 1 and a light emitter 7 located below the path so as to obtain print pattern data and watermark pattern data of the bill 1. The detected data are compared with the print pattern data and watermark pattern data of the true bill stored in a memory.

However, by the conventional bill validating apparatus, it is also difficult to detect and reject forged bills that are produced by color copying machines using transmitted light because the forged bills include watermark patterns therein. For carrying out more accurate validation, it is necessary to use an identification method for detecting magnetism included in ink of the bills and comparing it with magnetism patterns of true ones stored in a memory in combination with the above validation method using reflected or transmitted light.

Thus, a combination validation method requires various and a great amount of data on the true bank bills for comparison to the detected data. In addition, it is equally possible whether each bank bills is transferred to the sensor forward or backward with its right or reverse side, the bill validating apparatus must require data for such four kinds of insertion conditions.

Therefore, a so-called Multi-Currency Bill Validator that is capable of validating bank bills of a plurality of countries by one machine further requires a great amount of data in proportion to the number of bank bills to be processed therein. Accordingly, both a high-speed CPU and large capacity memories must be required to avoid lowering the operation speed to be caused by the above restrictions. Thus, the manufacturing cost has been inevitably high.

In addition, even in the case of bill validators provided with both large capacity memories and a high-speed CPU, there still remain problems of rejecting true bank bills due to noises derived from their folds or stains, and there also remain problem of mistaking forged bank bills for true ones because the magnetic characteristics of copying ink (toner) used in some color copying machines are similar to those of true bank bills.

SUMMARY OF THE INVENTION

Accordingly, the first object of the present invention is to provide a validator for bank bills, debentures, stock certificates, or the like objects, that is improved in ensuring good accuracy on validating such objects and enhancing the operation speed even in case of processing various kinds of objects.

The second object of the present invention is to provide a validator having light sensors, that can improve the validation accuracy and suppress noise effects due to stains, etc., on the objects without requiring a high-speed CPU and large capacity memories.

In order to achieve the first object described above, the present invention provides a validator for bank bills or the like objects including reading means for reading patterns on each object conveyed by conveying means to identify the object by comparing the read data with pattern data of true bills stored in advance in memory means, and outer dimension detecting means for detecting the outer dimensions of the object being conveyed by the conveying means, the memory means also having stored data on the outer dimensions of true bills and classified them into groups in advance, so that only the data corresponding to the detected outer dimension data are taken out from the memory means to compare them with the pattern data read by the pattern reading means.

In order to achieve the second object, the present invention provides a validator for bank bills or the like objects for validating whether they are true or not by reading watermark patterns of each object using two optical reading means respectively utilizing transmitted light and reflected light and comparing the data obtained from both the reading means.

Also the present invention provides a method of validating sheet paper objects by reading print patterns provided at the respective same positions on sheet paper objects using two optical reading means respectively utilizing infrared light and visible light and comparing the data outputted from both the reading means.

In addition, the present invention provides a method of validating sheet paper objects by reading print patterns on sheet paper objects using optical reading means utilizing infrared light and comparing the data obtained from the reading means with data of the corresponding true sheet papers stored in advance in memory means.

DETAILED DESCRIPTION OF THE INVENTION

Hereinafter, several embodiments of the present invention will be described with reference to the drawings.

Figures 1A, 1B:
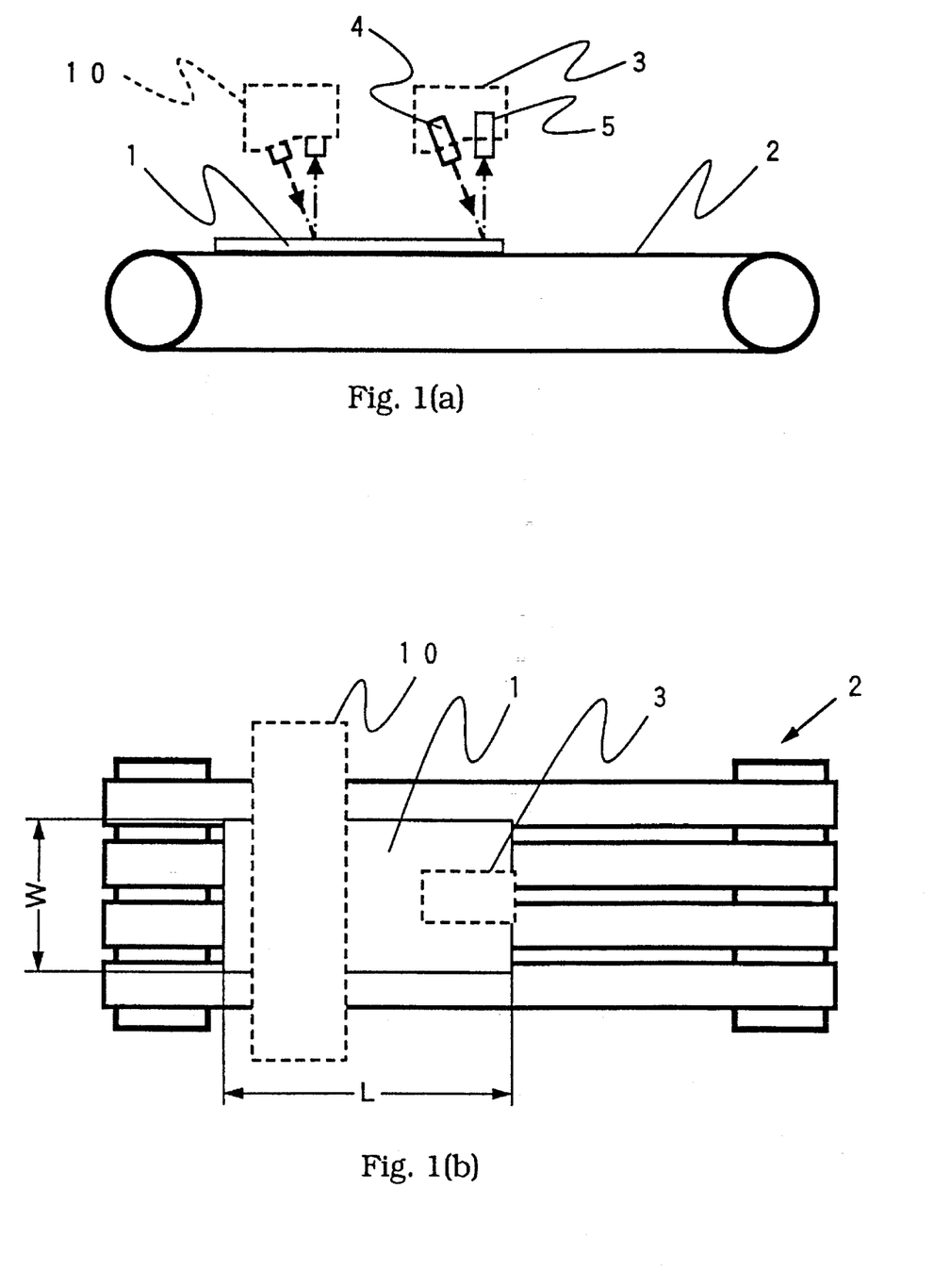
FIG. 1(a) is a side view showing a structure of the first embodiment of the validator for bank bills or the like objects relating to the present invention.
FIG. 1(b) is a plan view showing a structure of the first embodiment of the validator for bank bills or the like objects relating to the present invention.

FIGS. 1(a) and 1(b) are side and plan views respectively showing a structure of the first embodiment of the validating apparatus relating to the present invention. In FIGS. 1(a) and 1(b), reference numeral 10 denotes a dimension detecting portion such as a line sensor in which reflection light type photo-sensors are arranged in a row at a predetermined pitches. The sensor 10 is located at a fixed position over conveying means 2 to detect the dimensions on width and length of bank bill 1. The other structure and functions of the validating apparatus are the same as the conventional validator shown in FIG. 13(a).

Figure 2A:
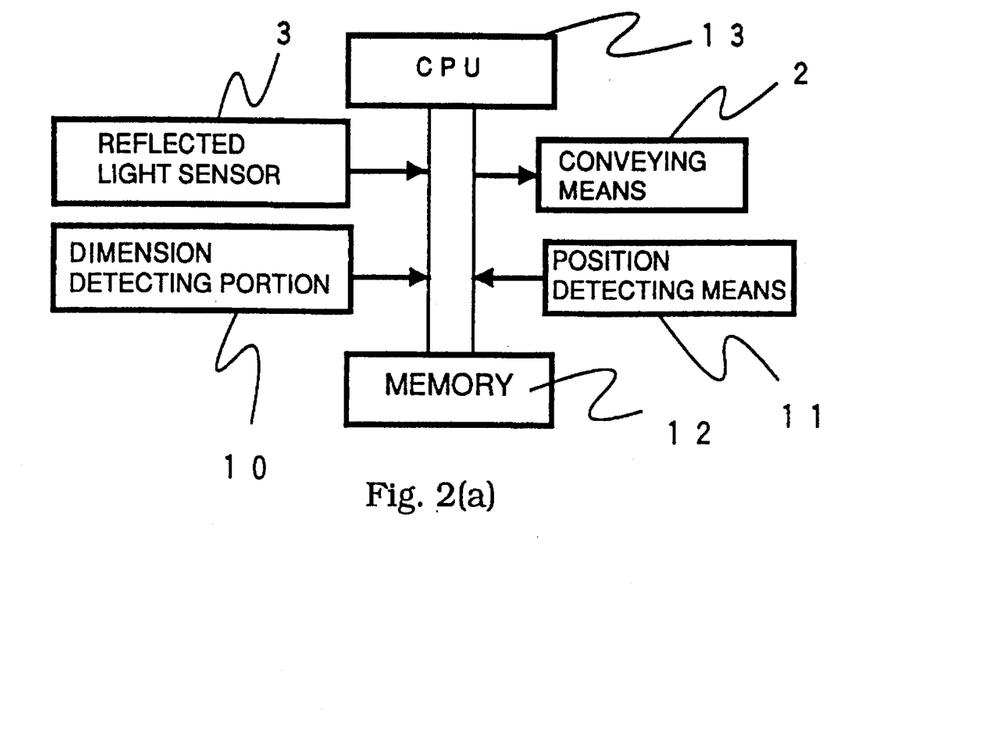
FIG. 2(a) is a block diagram showing an embodiment of the control system used in the present invention.

FIG. 2(a) is a block diagram showing a structure of the first embodiment of the control system. With reference to FIGS. 1(a), 1(b), and 2(a), the operation of the apparatus according to the present invention will be described.

Reference numeral 11 designates position detecting means such as a rotary encoder cooperatively associated with conveying means 2. When the edge of bank bill 1, which is conveyed from the left side in FIG. 1(a) and 1(b), reaches a position of the dimension detecting portion 10 just under the dimension detecting portion 10, sensors located near the central position detect the presence of the bank bill 1, and counting the number of pulses generated from the position detecting means 11 is started. Then the dimension data about length L of bank bills 1 is obtained by counting the number of pulses until the other edge of bank bill 1 passes the dimension detecting portion 10.

With such detection of length, some of the sensors disposed in the dimension detecting portion 10 corresponding to the width W of bank bill 1 detect the presence of the bank bill, but the others insensible thereto. Therefore, the dimension data on width of the bank bill can be also obtained by such construction.

Figure 2B:
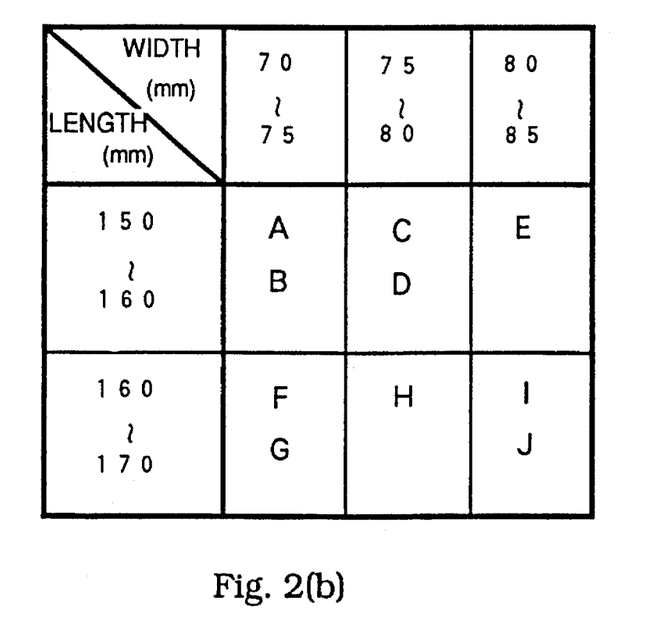
FIG. 2(b) shows an example of data classified into groups in a memory.

In memory 12, the dimensions on width and length of bank bills have been classified into groups A to J as shown in FIG. 2(b), and pattern data corresponding to each type of dimensions have been stored in the memory 12 in advance.

For example, when the dimension detecting portion 10 detects the dimensions of the bank bill 1 as L=152 mm and W= 76 mm, the detected bank bill 1 is classified into either group C or D. Accordingly, the validation from the pattern data on bank bill 1 obtained by reflection light sensor 3 will be possible only by carrying out eight matching steps with respect to two kinds of bank bill groups C and D by four kinds of insertion data, i.e., forward and backward directions and right and reverse sides. Thus, the bank bill 1 can be validated more rapidly with high efficiency than the conventional validating apparatus in which the matching steps must be carried out with respect to each of the ten types A to J.

By classifying the type of bank bills in advance, a plurality of currencies can be validated rapidly without using a high-speed CPU. In addition, more assured validation of bank bills can be performed by adopting the magnetic pattern detection method or print patten detection method having been known in common after the classification process described above.

Next, a validation means for detecting forged bank bills produced by a color copying machine will be described.

With respect to such a validation means, two cases that forged bank bills are produced by a color copying machine using magnetic material (toner) insensible to infrared light and that they are produced by a color copying machine using magnetic material (toner) sensible to infrared light must be considered.

First, the case in which forged bank bills are produced by a color copying machine using a toner insensible to infrared light is described.

In this case, like parts shown in FIGS. 1 and 2 are denoted by same reference numerals in all the drawings described below, and the explanations on those parts are thus omitted.

Figure 3:
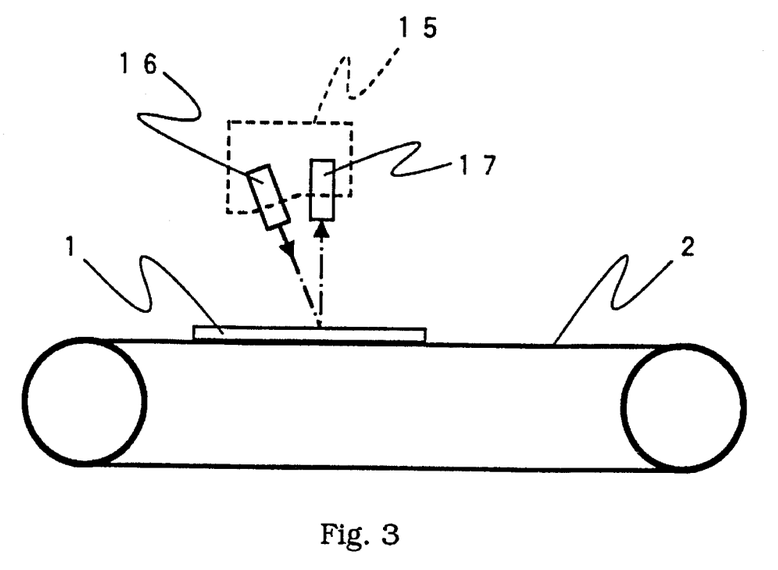
FIG. 3 shows a structure of the second embodiment of the validator for bank bills or the like objects relating to the present invention.
Figure 4:
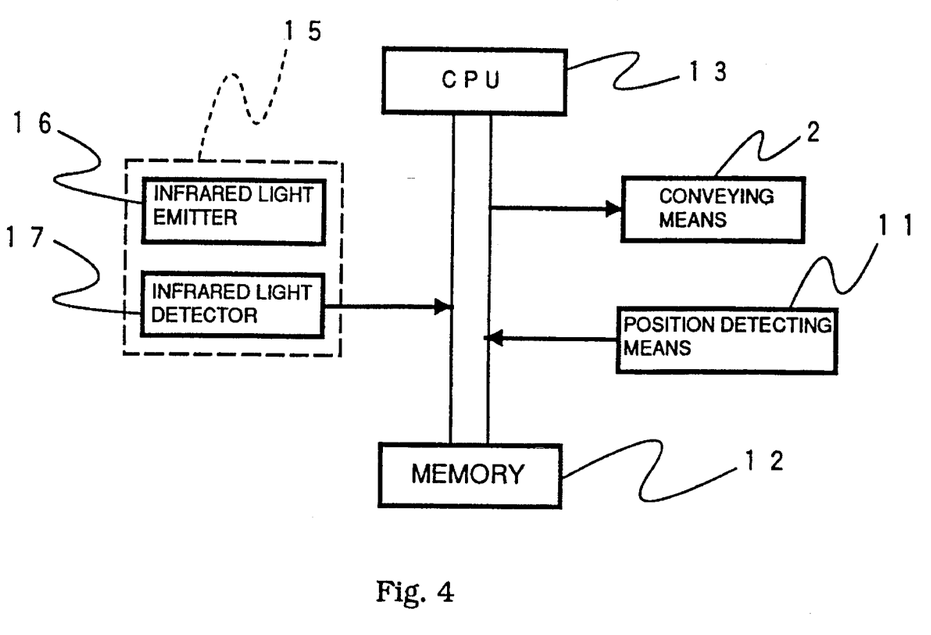
FIG. 4 is a block diagram showing an embodiment of the control system used in the embodiment shown in FIG. 3.

FIGS. 3 and 4 are a side view and a block diagram respectively showing the second embodiment of the validating apparatus for bank bills or the like objects.

This validating apparatus is comprised of a conveying means 2 such as a belt or the like, an infrared light sensor 15 provided at predetermined position over the conveying means 2. A bank bill 1 are transferred by the conveying means 2 and data on print patterns of the bank bill is detected by the infrared light sensor 15. The infrared light sensor 15 is controlled by the data from position detecting means 11 cooperatively associated with the conveying means 2 during conveyance of bank bill 1 for a predetermined transfer distance.

The detected data of the print patterns are compared with the data on print patterns of the true bills stored in advance in memory 12 using a CPU 13 to validate whether the object is true or not.

The infrared light sensor 15 is comprised of a light emitter 16 and a light detector 17. The light emitter 16 uses a light source such as an LED or the like elements capable of emitting a predetermined amount of infrared light. The infrared light emitted from the light emitter 16 is irradiated onto the bank bill 1 and is then reflected by the surface of the bank bill. Then the light detector 17 receives the reflected infrared light and converts it into an electric signal corresponding to the light amount. Since the amount of reflected light changes in response to the shades of colors of the print pattern, each pattern can be detected as an electric signal.

The principle of the validation according to this embodiment is based on the phenomenon that we found in which part or all of print patterns of forged bank bills produced by a specific color copying machine cannot be detected when the patterns are read by an infrared sensor in place of conventional visible light sensors.

Accordingly, it becomes possible to completely validate and reject such forged bank bills produced by a specific color copying machine using toner insensible to infrared light.

Figure 5A:
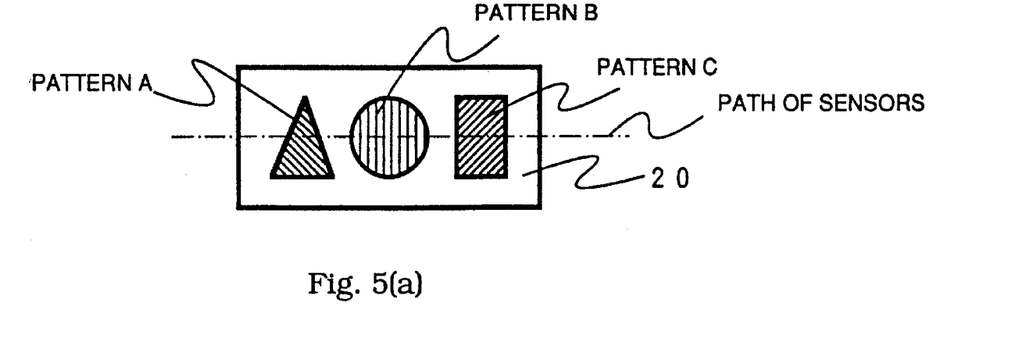
FIGS. 5(a) to 5(c) show detection data relating to the embodiment shown in FIG. 3, respectively.
Figure 5B:
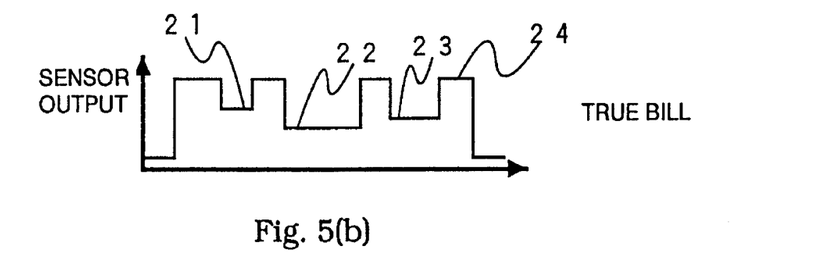

In case that a bank bill having, for example, three kinds of patterns A, B and C on its sheet paper 20 as shown in FIG. 5(a), the sensor 15 outputs a signal including levels 21 to 23 respectively corresponding to the patterns A, B, C and the background level 24 corresponding to the sheet paper 20 can be obtained as shown in FIG. 5(b) when a true one is inserted in the validating apparatus.

Figure 5C:
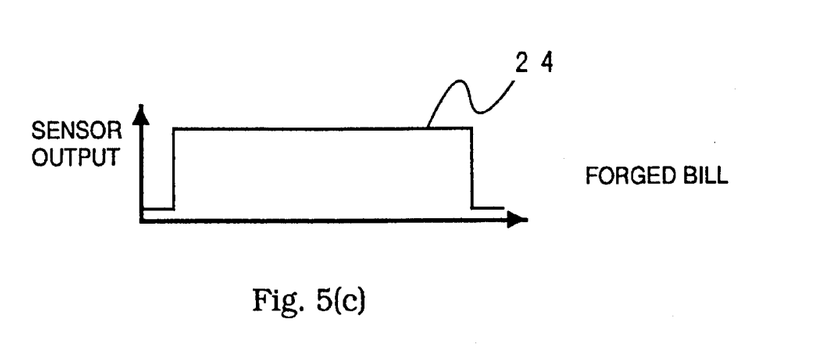

On the other hand, when a forged bank bill produced by the specific color copying machine is inserted, a signal including only the level 24 of the sheet paper 20 is outputted as shown in FIG. 5(c). Thus, such a forged bank bill can be discriminated easily and clearly.

However, in case that bank bills produced by another type of a color copying machine using toner sensible to infrared light, the sensor 15 outputs signal in which levels are similar to that of a true bill as shown in FIG. 5(b). Therefore, some forged bank bills may be mistaken for true ones depending on the type of color copying machine used for their forgery.

In such a case, the means for validating watermarks of bank bills may be used in combination with the embodiment described above.

Figure 6:
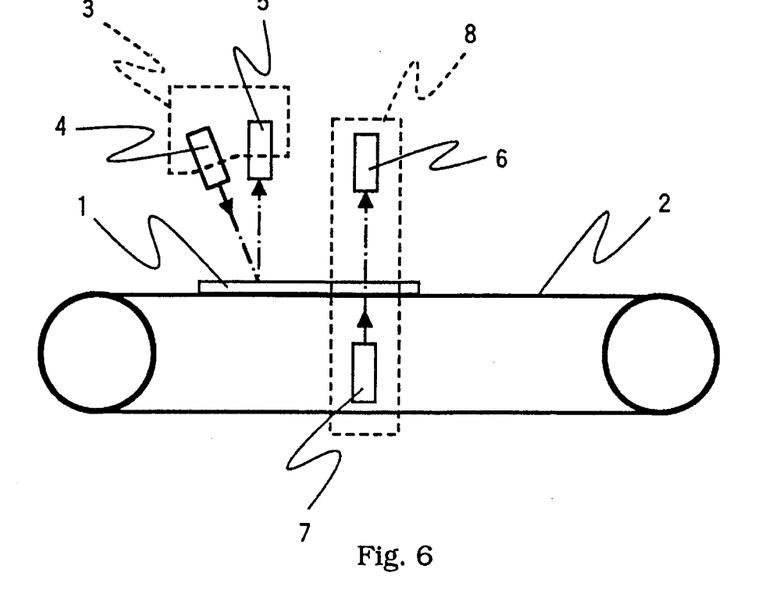
FIG. 6 shows a structure of the third embodiment of the validator for bank bills or the like objects relating to the present invention.
Figure 7:
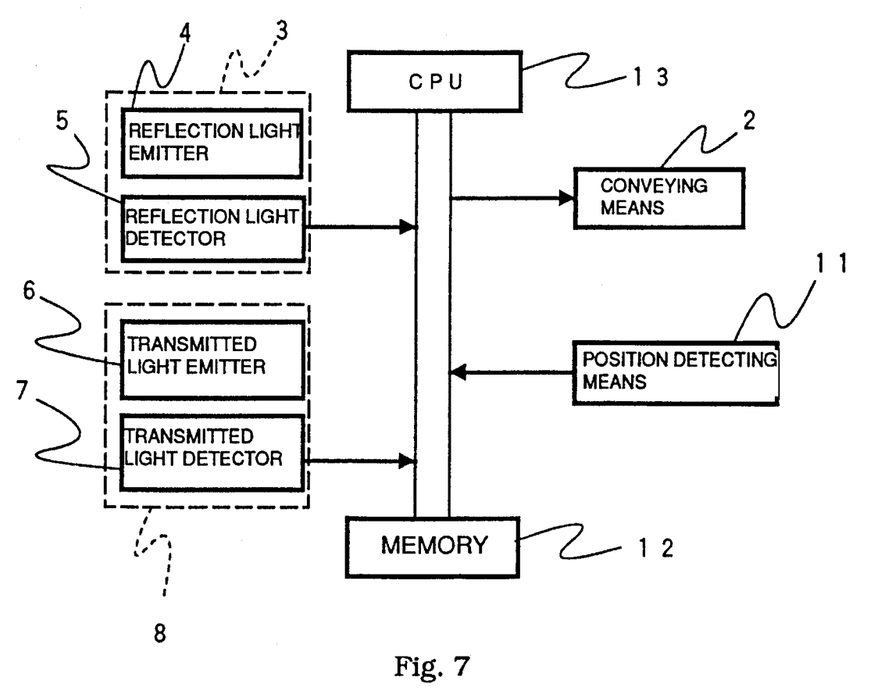
FIG. 7 is a block diagram showing an embodiment of the control system used in the embodiment shown in FIG. 6.

FIGS. 6 and 7 are a side view and a block diagram respectively showing the third embodiment of the validating apparatus relating to the present invention. The validating apparatus conveys a bank bill 1 inserted therein by conveying means 2 such as a belt or the like means and reads data on watermark patterns of the bank bill through a reflection light sensor 3 and a transmission light sensor 8 provided respectively at predetermined positions to the conveying means 2. The reflection light sensor 3 and transmission light sensor 8 are controlled by data from the position detecting means 11 cooperatively associated with the conveying means 2 during conveyance of the bank bill 1 for a predetermined transfer distance.

In that case, both sensors 3 and 8 are arranged in a row and parallel with the conveying direction of the bank bill 1 to read its print patterns of the same positions. Thus, the data outputted from both sensors are compared by a CPU 13.

Figure 8A:
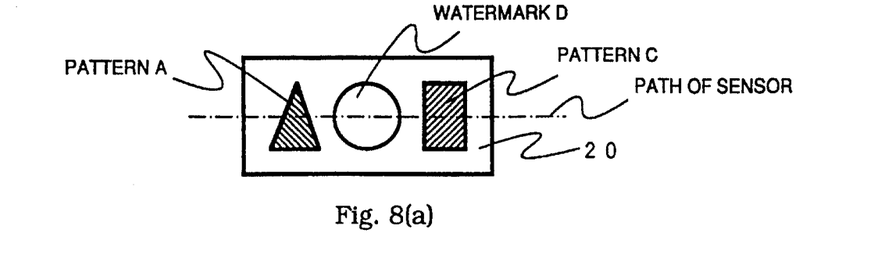
FIGS. 8(a) to 8(g) show detection data relating to the embodiment shown in FIG. 6, respectively.
Figure 8B:
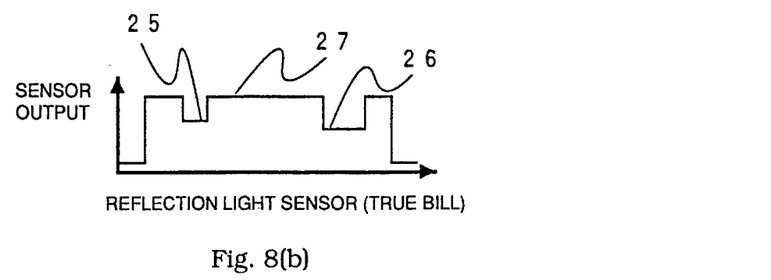

In case of the bank bill having, for example, two patterns A, C and one watermark D on its sheet paper 20 as shown in FIG. 8(a), when a true bank bill is inserted in the validator, the sensor 3 outputs a signal including levels 25, 26 respectively corresponding to the patterns A, C and level 27 corresponding to the sheet paper 20 since the reflection light sensor 3 detects only the print patterns on the surface as shown in FIG. 8(b).

Figure 8C:
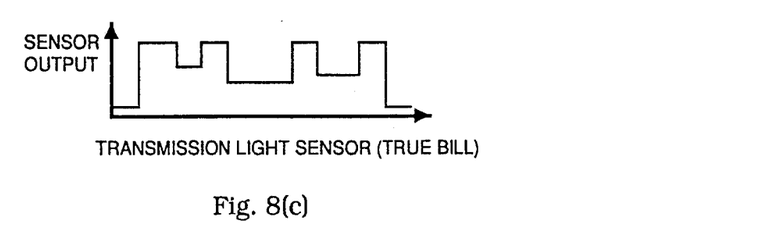

On the other hand, the transmission light sensor 8 outputs a signal including the pattern of the watermark D with the print patterns as shown in FIG. 8(c). Thus, the inserted bank bill is validated as a true one because the output data on the portion corresponding to watermark D from both sensors 3 and 8 do not coincide with each other in the CPU 13.

Figure 8D:
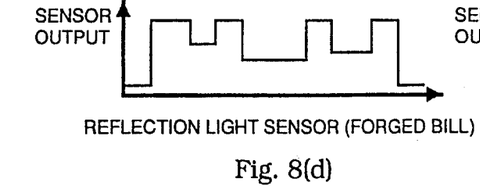
Figure 8E:
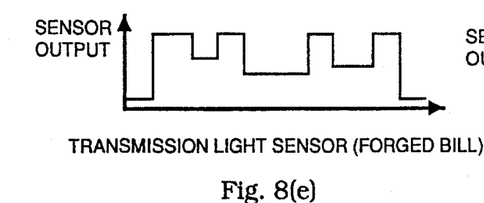
Figure 8F:
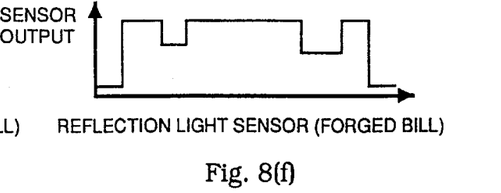
Figure 8G:
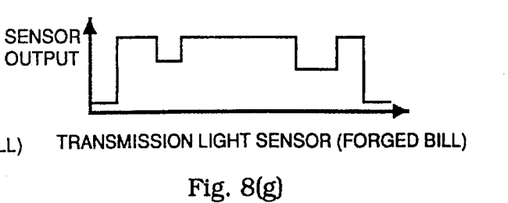

On the contrary, when a forged bank bill produced by a transmission light type color copying machine is inserted to be validated, the output data from both sensors 3 and 8 on the portion corresponding to the watermark D coincide with each other as shown in FIGS. 8(d) and 8(e). Likewise, in case of a forged bank bill produced by a reflection light type color copying machine, the output data from both sensors 3 and 8 on the same portion corresponding to the watermark D also coincide with each other as shown in FIGS. 8(f) and 8(g). Thus, the inserted bank bill can be validated and rejected as forged one when these data are the same as each other.

The validation method using both transmitted light and reflected light to validate the water mark of a bank bill is not limited to use in combination with the validation method using infrared light as described above but may be used as independent an validating function.

Further, in case that bank bills, such as Taiwanese dollar bills, use both two kinds of ink sensible and insensible to infrared light, the validating means described below is also effective.

Figure 9:
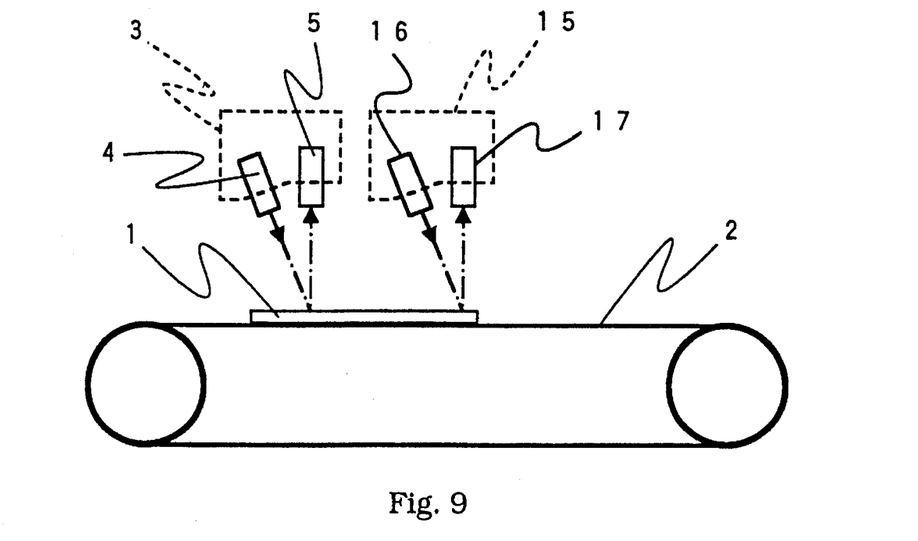
FIG. 9 shows a structure of the fourth embodiment of the validator for bank bills or the like objects relating to the present invention.
Figure 10:
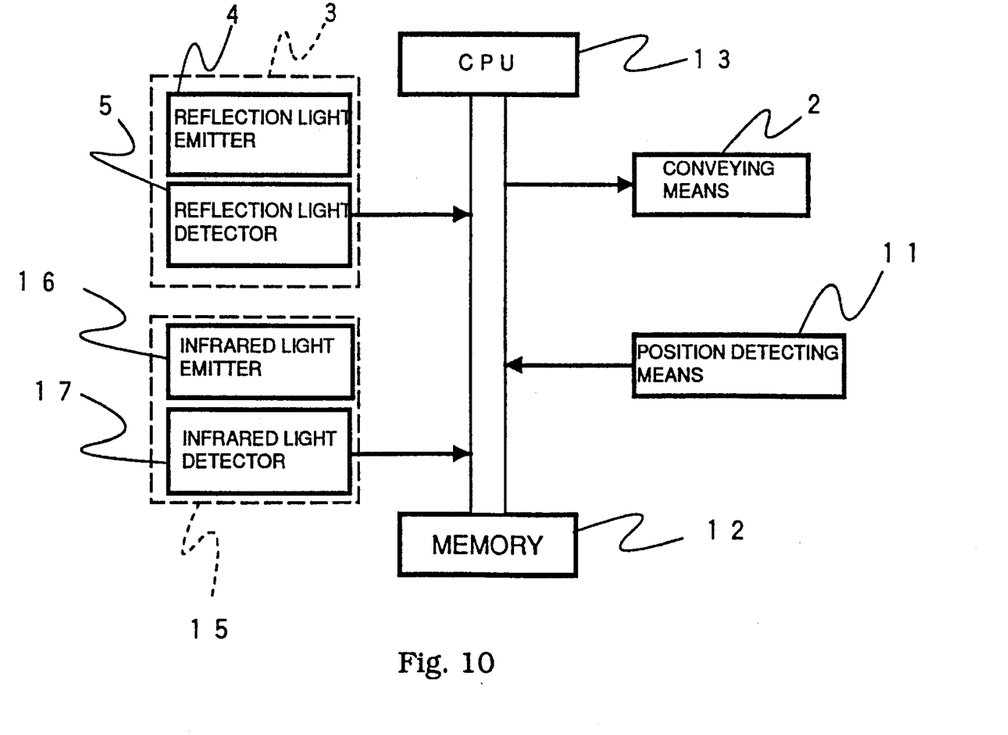
FIG. 10 is a block diagram showing an embodiment of the control system used in the embodiment shown in FIG. 9.

FIGS. 9 and 10 are a side view and a block diagram respectively showing the fourth embodiment of the validating apparatus relating to the present invention. This validating apparatus is comprised of an infrared light sensor 15 and a visible light sensor 3.

As shown in FIGS. 9 and 10, the validating apparatus of this embodiment reads data on print patterns of a bank bill 1 through the visible light sensor 3 and the infrared light sensor 15. These sensors 3 and 15 are controlled by the data from the position detecting means 11 cooperatively associated with the conveying means 2 during conveyance of bank bills 1 for a predetermined transfer distance.

In such case, both sensors 3 and 15 are arranged in a row and parallel with the conveying direction of the bank bill 1 to read its print patterns of the same positions. Then, the data outputted from both sensors are compared by a CPU 13.

The infrared light sensor 15 is comprised of a light emitter 16 and a light detector 17. The light emitter 16 uses a light source such as an LED or the like elements capable of emitting a predetermined amount of infrared light. The infrared light emitted from the light emitter 16 is irradiated onto the bank bill 1 and is then reflected by the surface of the bank bill 1.

Then the light detector 17 receives the reflected infrared light and converts it into an electric signal corresponding to the light amount. Since the amount of reflected light changes in response to shades of colors of the print pattern, each pattern can be detected as an electric signal.

Thus, if a classifying apparatus for classifying the type of bank bills, which is disposed on a previous stage to the validator, detects the inserted bank bill as a special bill using both kinds of ink insensible and sensible to infrared light for its patterns, a forged bank bill can be validated by the validating apparatus described above.

That is, when a true bank bill is inserted in such a validator, the visible light sensor 3 can detect its print patterns completely, but the data from the infrared light sensor 15 does not detect all of the patterns. Thus, both sensor outputs on the pattern portion insensible to infrared light do not coincide with each other in comparison by a CPU 13.

However, in case that a forged bank bill produced by a color copying machine or the like means, both sensor outputs are the same as each other, thereby validating and rejecting the inserted bank bill as forged one.

Figure 11A:
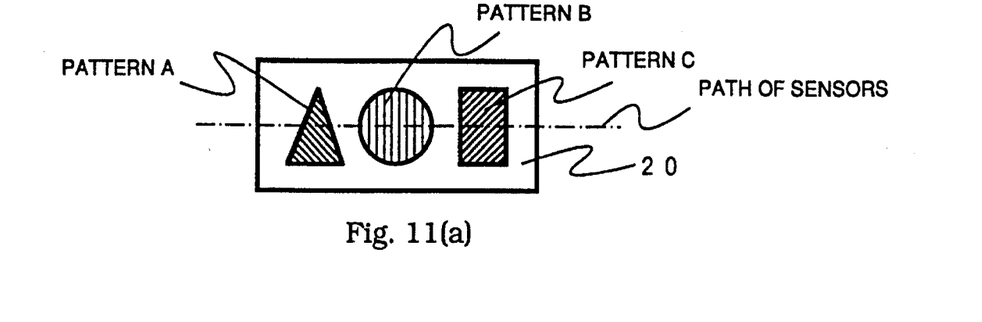
FIGS. 11(a) to 11(e) show detection data relating to the embodiment shown in FIG. 9, respectively.
Figure 11B:
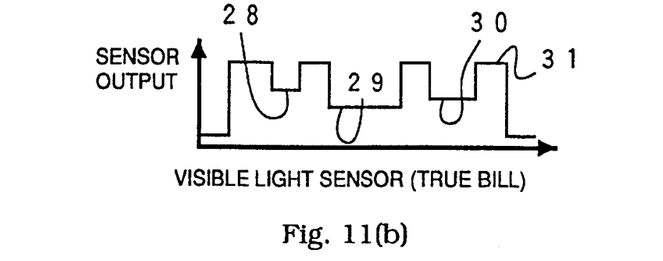
Figure 11C:
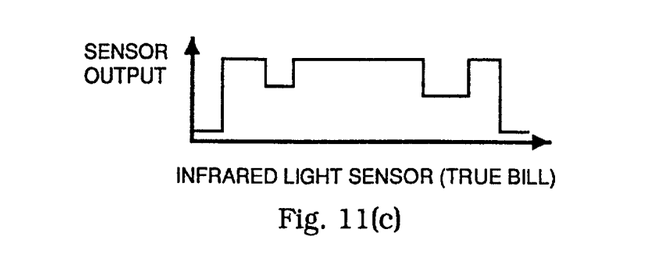

In case that a bank bill having, for example, three kinds of patterns A, B and C on its sheet paper 20 in which the pattern B is insensible to infrared light as shown in FIG. 11(a), when a true bank bill is inserted in the validator, the visible light sensor 3 outputs a signal including levels 28 to 30 respectively corresponding to patterns A, B, C, and level 31 corresponding to the sheet paper 20 as shown in FIG. 11(b). On the other hand, the level corresponding to pattern B does not appear in the output signal from the infrared light sensor 15 as shown in FIG. 11(c). Thus, the component of level 29 can be detected by comparing both two outputs.

Figure 11D:
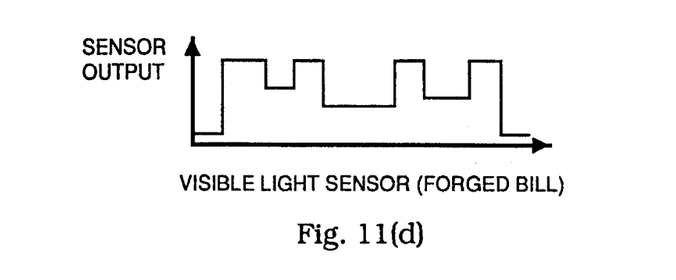
Figure 11E:
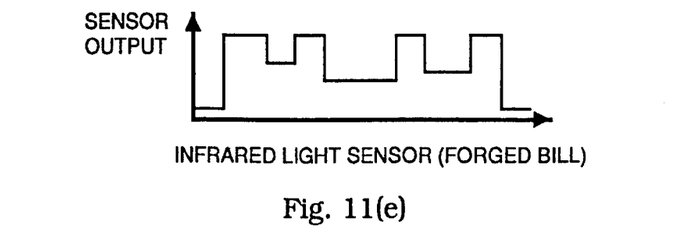

On the contrary, when a forged bank bill produced by the specific color copying machine or the like means is inserted, both sensor outputs coincide with each other as shown in FIGS. 11(d), 11(e). Thus, the difference becomes zero, and the bank bill can be validated as forged one easily and clearly.

Figure 12:
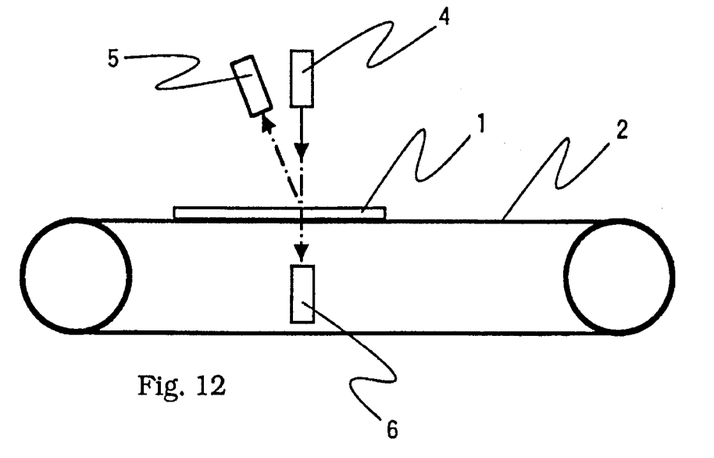
FIG. 12 shows a modified example of the third embodiment.

In addition, it can be apparently understood that similar result can be obtained by constructing the validating apparatus with three elements, a common light emitter 4, a light detector 5 for receiving reflected light and a light detector 6 for receiving transmitted light, as shown in FIG. 12.

As described in the second embodiment, even in case of a forged bank bill having print patterns produced by a specific color copying machine to be recognizable as patterns by visible light but recognized as unprinted by infrared light, the sensor mechanism may be substituted with a so-called transmission light type sensor wherein the light beams of both visible light sensor 3 and infrared light sensor 15 shown in FIG. 9 are transmitted through the bank bills, otherwise only the light beam of the infrared light sensor 15 of these two sensors is transmitted therethrough.

Additionally, in the event that the object is validated as a specific one whose all print patterns are insensible to infrared light by the classifying apparatus, the sensor mechanism may be constructed to read watermark patterns of the bank bills by a sensor and compare them with data on the watermark patterns of the true one stored in a memory, thereby being discriminatable even to the forged ones produced by such a special color copying machine.

That is, by replacing only the transmission light sensor 8 shown in FIG. 6 with an infrared light sensor to detect watermark patterns of a bank bill when it is detected as a specific bank bill by the classifying apparatus and comparing them with the patterns of the true bank bill, it becomes possible to enhance the accuracy of validation between forged and true bank bills with a simple structure.

As stated above, according to the present invention, the ability of the apparatus for validating whether a bank bill is a true one or not can be enhanced only by adopting two optical sensors with relatively simple construction. Since the validation can be completed by comparing only the outputs from the two optical sensors, it is not necessary to prepare a great amount of data for the comparison. Thus, the memory capacity can be reduced to the minimum.

In addition, the principle of validation according to the present invention is not based on the comparison between the data obtained from an object and those stored in advance in a memory as is seen in the prior art, but based in essence on the comparison between the data from one object via two kinds of sensor means. Therefore, noises caused by folds and stains of a bank bill or the like object can be canceled by these two kinds of data from the same object.

In addition, the enhancement of ability of such an optical sensor type identifier with relatively simple construction leads to reduction of load to be imposed on the other methods cooperatively associated with the apparatus, thereby reducing the operation speed and ability of CPU to the minimum.

Although only the construction for validating whether a bank bill is true or forged is described above, the present invention is not limited to this object. That is, this invention can be also applied to identification of watermark patterns on stocks and bonds or the like securities other than the bank bills.

We claim:

1. A multi-currency bill validating apparatus comprising:

a pattern reading means for reading a pattern on bank bills and for generating data corresponding to said pattern, said pattern reading means comprising:
light emitting means for generating a beam of visible light and emitting said visible light onto the surface of said bank bills; and
a light detecting means for detecting reflected light from said bank bills;

a conveying means for transferring said bank bills to a predetermined position;

an outer dimension detecting means for detecting an outer dimension of said bank bills, said outer dimension detecting means comprising a light emitting means, a light detecting means and a position detecting means;

a memory means for storing data in which a plurality of currency data is classified into a plurality of groups by outer dimensions of said bank bills;

a means for selecting data corresponding to a group of the same outer dimensions from said memory means based on the data detected by said outer dimension detecting means; and a means for comparing only the selected data with the data read by the pattern reading means for validating said bank bills.

* * * * *

UNITED STATES PATENT AND TRADEMARK OFFICE
CERTIFICATE OF CORRECTION

PATENT NO. : 5,483,069
DATED : January 9, 1996
INVENTOR(S) : SHINICHI KOFUNE and KENYA KAWABE It is certified that error appears in the above-indentified patent and that said Letters Patent is hereby corrected as shown below:

On the title page, insert item [30] as follows:

FOREIGN APPLICATION PRIORITY DATA

Dec. 25, 1992   [JP]   Japan   ................   4-359633
Dec. 25, 1992   [JP]   Japan   ................   4-359634
Dec. 25, 1992   [JP]   Japan   ................   4-359635
Dec. 25, 1992   [JP]   Japan   ................   4-359636

Signed and Sealed this

Fourteenth Day of May, 1996

Attest:

BRUCE LEHMAN

Attesting Officer        Commissioner of Patents and Trademarks